United States Patent
Gupta et al.

(10) Patent No.: US 12,408,884 B2
(45) Date of Patent: Sep. 9, 2025

(54) SYSTEM AND METHOD FOR X-RAY ELASTOGRAPHY USING DYNAMIC PULSING

(71) Applicant: The General Hospital Corporation, Boston, MA (US)

(72) Inventors: Rajiv Gupta, Wayland, MA (US); Chika Kamezawa, Boston, MA (US); Avilash Cramer, Cambridge, MA (US); Wolfgang Krull, Boxford, MA (US); Wataru Yashiro, Boston, MA (US); Kazuyuki Hyodo, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 211 days.

(21) Appl. No.: 18/067,517

(22) Filed: Dec. 16, 2022

(65) Prior Publication Data

US 2023/0190214 A1 Jun. 22, 2023

Related U.S. Application Data

(60) Provisional application No. 63/290,609, filed on Dec. 16, 2021.

(51) Int. Cl.
*A61B 6/00* (2024.01)
*A61B 6/46* (2024.01)

(52) U.S. Cl.
CPC ............. *A61B 6/486* (2013.01); *A61B 6/461* (2013.01); *A61B 6/5217* (2013.01); *A61B 6/5258* (2013.01); *A61B 6/542* (2013.01)

(58) Field of Classification Search
CPC ......... A61B 6/461; A61B 6/482; A61B 6/486; A61B 6/5217; A61B 6/5258; A61B 6/542; A61B 5/0051
See application file for complete search history.

(56) References Cited

U.S. PATENT DOCUMENTS 9,775,575 B2 * 10/2017 Proksa ................. A61B 6/5205
10,895,540 B1    1/2021 Gupta et al.
(Continued)

OTHER PUBLICATIONS

Cramer et al., Stationary Computed Tomography for Space and Other Resource-Constrained Environments, Scientific Reports, 2018, 8:14195, pp. 1-10.

*Primary Examiner* — David J Makiya
*Assistant Examiner* — Soorena Kefayati
(74) *Attorney, Agent, or Firm* — QUARLES & BRADY LLP

(57) ABSTRACT

X-ray absorption of breast cancers and surrounding healthy tissue can be very similar, a situation that sometimes leads to missed cancers or false-positive diagnoses. To increase the accuracy of tomosynthesis and cancer diagnosis, dynamic X-ray elastography using a novel pulsed X-ray source synchronized to shear waves generated in a sample is described in the present disclosure. This imaging modality provides both absorption and mechanical properties of the imaged sample. A vibration source is used to vibrate the sample while a synchronously pulsed cold cathode X-ray source images the mechanical deformation. The generated stroboscopic images are further used to derive stiffness maps of the sample in addition to the conventional X-ray image.

18 Claims, 10 Drawing Sheets

(56) References Cited

U.S. PATENT DOCUMENTS

| | | | |
|---|---|---|---|
| 2006/0002514 A1* | 1/2006 | Dunham | A61B 6/4014 |
| | | | 378/119 |
| 2012/0226158 A1* | 9/2012 | Greenleaf | G01S 7/52022 |
| | | | 600/438 |
| 2015/0216496 A1* | 8/2015 | Lee | A61B 6/5217 |
| | | | 600/425 |
| 2015/0335281 A1* | 11/2015 | Scroggins | A61B 5/055 |
| | | | 600/410 |
| 2016/0014344 A1* | 1/2016 | Yoo | H04N 23/80 |
| | | | 345/420 |
| 2016/0213341 A1* | 7/2016 | Salcudean | A61B 6/50 |
| 2016/0274210 A1* | 9/2016 | Sack | A61B 5/055 |
| 2017/0238884 A1* | 8/2017 | Jeong | A61B 5/0051 |
| 2017/0333005 A1* | 11/2017 | Chen | A61B 8/485 |
| 2018/0125442 A1* | 5/2018 | Kolipaka | A61B 6/5235 |
| 2018/0328798 A1* | 11/2018 | Silver | G01L 1/103 |
| 2019/0178821 A1* | 6/2019 | Morton | H01J 35/08 |
| 2019/0252148 A1* | 8/2019 | Travish | H01J 35/065 |
| 2019/0254634 A1* | 8/2019 | Honjo | A61B 8/5223 |
| 2019/0320992 A1* | 10/2019 | Koyakumaru | A61B 8/08 |
| 2020/0054217 A1* | 2/2020 | Parker | A61B 5/7239 |
| 2021/0137469 A1* | 5/2021 | Zhao | A61B 6/469 |

* cited by examiner

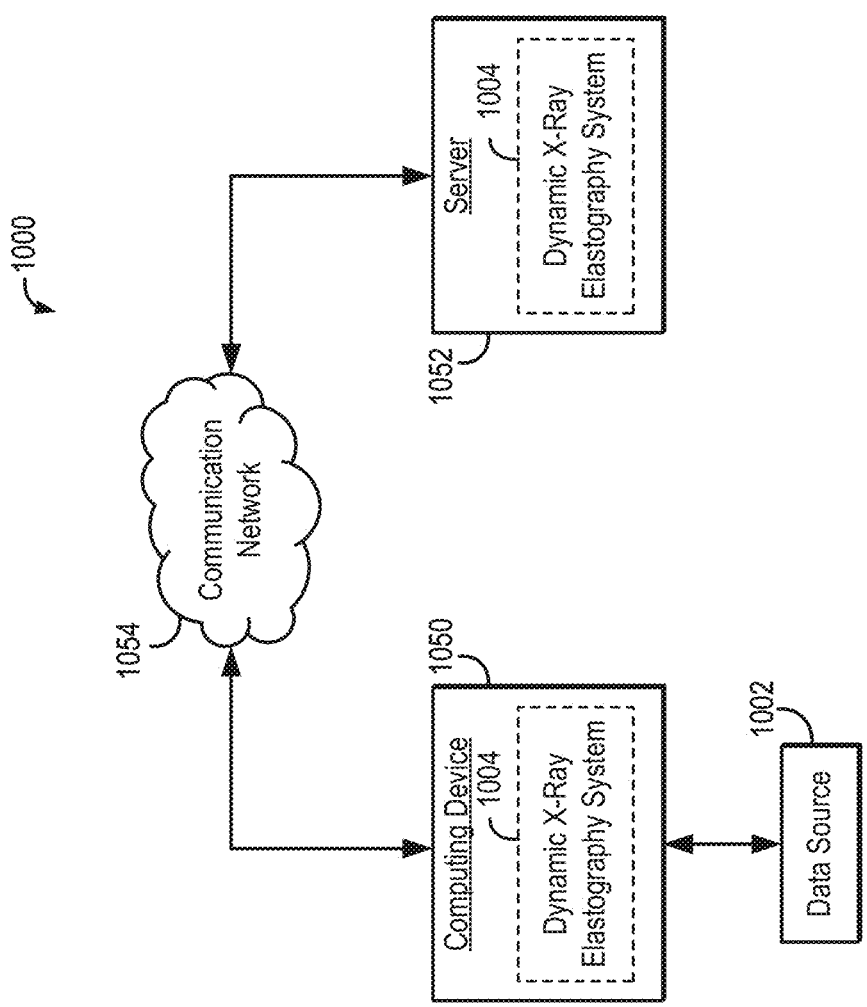

SYSTEM AND METHOD FOR X-RAY ELASTOGRAPHY USING DYNAMIC PULSING

CROSS-REFERENCE TO RELATED APPLICATIONS

This application is based on, claims priority to, and incorporates hereby reference in its entirety for all purposes U.S. Provisional Application Ser. No. 63/290,609, filed Dec. 16, 2021, and entitled, "Dynamic X-ray elastography using a pulsed photocathode source."

STATEMENT REGARDING FEDERALLY SPONSORED RESEARCH

N/A

BACKGROUND

Tissue elastography, a noninvasive imaging modality used to assess tissue stiffness, has been under development for the past three decades. Because cancerous lesions have different mechanical properties than adjacent healthy tissue, elastography aims to detect such lesions based on their stiffness. Even when such lesions have similar X-ray attenuation to the surrounding tissue, and are therefore not apparent on conventional mammography, elastography may be able to detect them.

There are two main classes of elastography techniques: static, and dynamic. In static elastography, a fixed static pressure is applied to the tissue under investigation and local strain from tissue deformation is mapped by imaging. This method can qualitatively evaluate the pattern of deformation and identify lesions. Static elastography, however, does not provide a quantitative map of tissue stiffness because it lacks a direct measure of the stress field within the tissue. Dynamic elastography uses shear wave propagation to map both stress and strain in the tissue in response to dynamic mechanical deformation, producing a quantitative elasticity map.

In dynamic elastography, shear waves are generated inside a sample by a superficially applied, time varying pressure. Such a pressure could be generated using air vibration, force impulse from acoustic radiation, or other methods that impart a shear wave which travels within the tissue. The time-varying stress and strain generated by this shear wave are continuously imaged. Using the observed image sequence, a quantitative elasticity map is generated by inferring the spatial and temporal variation in the tissue displacement from the velocity of the propagating shear wave. Depending on the sample of interest, a number of different medical imaging techniques may be employed to image the shear wave. Both magnetic resonance (MR) and ultrasound (US) elastography have rapidly expanded into clinical practice and have been used for liver and breast diseases, respectively. In recent years, elastography studies have also been reported in optical coherence tomography and photoacoustic imaging.

Despite higher spatial resolution and superior penetration depth of X-rays compared with other imaging modalities, there are relatively few examples of X-ray elastography. In the past decade, static elastography using X-ray imaging has been reported. As mentioned before, these static techniques do not provide a quantitative elasticity information.

Accordingly, there is a continuing need for systems and methods to gather quantitative information about tissue in clinical situations that call for X-ray imaging.

SUMMARY

The present disclosure addresses the aforementioned drawbacks via methods and systems for dynamic X-ray elastography that synchronize X-ray pulses with shear waves that are generated to propagate through tissue being imaged by the X-rays. A dynamic X-ray elastography method and an apparatus for implementing it using a pulsed X-ray source is described. This imaging modality provides both absorption and mechanical properties of the imaged material by vibrating the sample while a synchronously pulsed cold cathode X-ray source images the mechanical deformation. Using the acquired stroboscopic images, stiffness maps of the sample in addition to the conventional X-ray image can be produced.

Accordingly, aspects of the present disclosure provide methods and systems that interrogate tissues using radiographic and dynamic elastography, which have significant advantages over conventional radiography and elastography modalities.

In an aspect of the present disclosure, a method for performing dynamic X-ray elastography is described, the method comprising: generating shear waves in a region of interest of a subject using a vibration source; generating X-rays from an X-ray source and directing the X-rays toward the region of interest of the subject; detecting X-rays using an X-ray detector and generating X-ray images of the region of interest; and generating, using a processor, two-dimensional stiffness maps from the X-ray images.

In an aspect of the present disclosure, an apparatus for performing dynamic X-ray elastography is described, the apparatus comprising: a vibration source; an X-ray source; an X-ray detector; and a processor configured to: drive the vibration source to generate shear waves in a region of interest of a subject; drive the X-ray source to generate and direct the X-rays toward the region of interest of the subject; generate one or more X-ray images from the X-ray detector; and generate two-dimensional stiffness maps from the one or more X-ray images.

BRIEF DESCRIPTION OF THE DRAWINGS

FIG. 10 is a block diagram of a system for implementing aspects of the systems and methods of the present disclosure.

DETAILED DESCRIPTION

According to aspects of the present disclosure, a dynamic X-ray elastography systems is described. The system may include an X-ray imaging module having an X-ray source within a vacuum manifold, equipped with a non-thermionic cathode that can reduce image scan time (and hence, motion artifacts), or delivered dose, through under-sampled acquisition sequences, and without adding additional sources. The non-thermionic nature of the cathode enables rapid on/off switching of X-rays without concern as to the thermal mass or the thermal time-constant of the cathode. The X-ray imaging module can be controlled to emit X-ray pulses synchronized to a vibration source that generates a shear wave in a sample under investigation, such that both absorption and mechanical properties are acquired.

According to another aspect of the present disclosure, a dynamic X-ray elastography method is described for extracting mechanical tissue properties from time-resolved images of the sample investigated by a dynamic X-ray elastography system.

Figure 1:
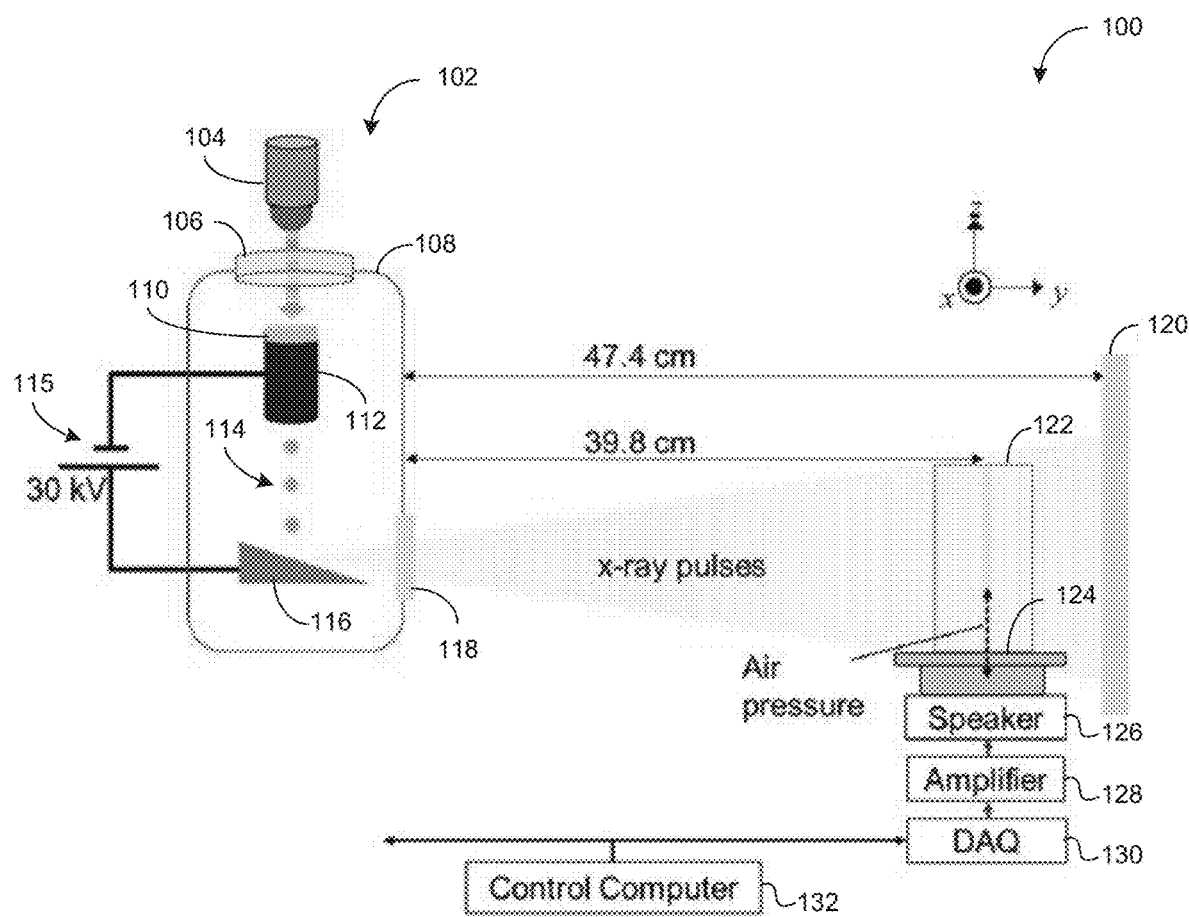
FIG. 1 is a schematic of a system for dynamic 2D X-ray elastography, according to aspects of the present disclosure.

According to aspects of the present disclosure, FIG. 1 schematically illustrates one non-limiting example system for dynamic X-ray elastography 100 using a compact pulsed X-ray source 102. The X-ray or radiation source 102 is designed to direct an X-ray beam, which may be a series pulses, toward a detector 120. As will be described, the X-ray or radiation source 102 may take any of a variety of forms, such as including ultraviolet (UV) light emitting diode (LED), a photocathode, or an electron amplifier. The radiation source may include a carbon nanotube forming a cathode. The radiation source may additionally or alternatively include a silicon field emitter forming a cathode.

In one non-limiting example, the X-ray source 102 may include an illumination source 104. The illumination source 104 may be designed to direct light toward a window 106, such as a quartz window. More particularly, the illumination source 104 may direct a pulsed light toward the window 106 and a photocathode 110. As one non-limiting example, the illumination source may include a light emitting diode (LED), that is selected to achieve a high frequency switching. The LED may operate in the ultraviolet (UV) range. For example, the LED may be a 255 nm, UV LED. The photocathode 110 may be a magnesium cathode, where magnesium (i.e., a magnesium thin film) is exposed to UV light from the illumination source 104 to produce electrons (e⁻) via the photoelectric effect. Magnesium has a relatively high quantum efficiency (QE) at the chosen UV wavelength, is abundant, and has few special handling concerns. In addition to magnesium, other metals or photo-sensitive bi-alkaline materials may be utilized. For example, the material may be selected to have a similar response at different frequency profiles.

In one non-limiting example, field emission could be used to generate electrons, by exposing a set of nano-sharp tips (not shown) to an electric field that overcomes the work function of the material of the cathode. Both photo and field emission x-ray sources have the desirable property that they can be turned on or off rapidly.

The electrons which pass through the photocathode 110 are received by a multi-channel plate or electron multiplier 112, such as a glass electron multiplier or Channeltron-type device, and may be amplified under a multiplier bias voltage (not shown). Electron amplification multiplies the number of electrons produced in the electron generation stage by the electron multiplier 112. In one configuration, the photocathode 110 may be a thin film photocathode deposited on an electron multiplier 112.

In one configuration, after amplification, the increased number of electrons from the electron multiplier 112 may result in an amplified electron beam 114 that is then accelerated through a high voltage (for example, high voltage difference 115, which may be on the order of 10-40 kV) and is incident upon an anode 116. Specifically, the electrons outputted from the electron multiplier 112 are accelerated as they fall down the voltage gradient between the photocathode 110 and anode 116. In medical X-ray tomography, tube voltages are often between 22 kVp (digital breast tomography) and 140 kVp (such as in a pelvic CT). The voltage level of the anode determines the energy spectrum of the X-rays produced by the source. Alternatively, electrons can be accelerated using a set of resonant radio frequency (RF) cavities, especially if higher voltages (6-25 MVp) are desired. In one configuration, the material of the anode 116 may be metal, such as tungsten, a tungsten alloy including a tungsten-rhenium alloy, molybdenum, rhodium, or other material with a high atomic number.

The photocathode and anode may both be contained within a vacuum manifold 108, which may be pumped down to, for example, $10^{-7}$ Torr, such as by using a turbo pump. The output electrons of the photocathode 110 are accelerated through a high voltage difference 115 to a anode 116, which may be a tungsten target anode, producing X-ray pulses through the Bremsstrahlung process. The electron beam from the electron multiplier 112 interacts with the anode 116, which produces the high energy X-rays. Specifically, accelerated electrons striking the anode 116 will emit X-rays over a range of energies dependent on the energy of the incident electrons and the energy levels of various electron shells of the target material (e.g. tungsten) of the anode 116.

In the above-described, non-limiting example, reflection-type X-ray generation is performed. The anode surface of the anode 116 may be angled or may have an angled surface with respect to the incident electron beam 114 in order to control the cone angle of the emitted X-rays. However, the systems and methods provided herein are not limited to only generating X-rays using reflection-type system, or the particular system described above. Any of a variety of X-ray/radiation sources may be utilized.

In one configuration, the X-ray output emanating from the anode 116 comes out of the vacuum manifold 108 through a window 118 that is nearly X-ray transparent. In one configuration, the window 118 may be covered with a thin, low atomic number element such as beryllium or aluminum. In one configuration, the window 118 may be composed of beryllium due to its low atomic number (z=4) and relative stability in atmosphere.

In one configuration, the X-ray pulses pass through a sample 122 to be imaged (for instance, a patient), and are recorded by a detector array 120. The detector array 120 may be a flat-panel detector or other detector configuration.

In one configuration, the X-ray source 102 may be a non-rotating tomographic imaging system, including a multi-source X-ray imaging module, which includes multiple X-ray sources 102 within a vacuum manifold, each equipped with a non-thermionic cathode.

A non-limiting example of a pulsed X-ray system is presented in U.S. Pat. No. 10,895,540, the contents of which are herein incorporated by reference.

In one configuration, the X-ray pulses are directed toward the sample 122. The sample 122 vibrated using a vibration source 126 to generate shear waves. The vibration source 126 may be a speaker to pneumatically vibrate the sample 122. The vibration source 126 may be integrated into a support surface 124 or be separately arranged to deliver the vibrations to the sample 122, which may be a subject or patient.

In one configuration, the vibration source 126 may be powered by a data acquisition module (DAQ) 130 or other suitable device, for generating a sinusoidal signal. An amplifier 128 may be used to amplify the signal being supplied to the vibration source 126 from the DAQ 130.

In one configuration, the X-ray pulses are synchronized with the shear wave generated in the sample 122 by the vibration source 126. For example, the control computer 132 may control timing or gating of the X-ray pulses and shear wave, respectively. The X-ray images are generated from X-rays detected as X-ray data by the flat-panel detector 120 at different phases of the shear wave.

Figure 2:
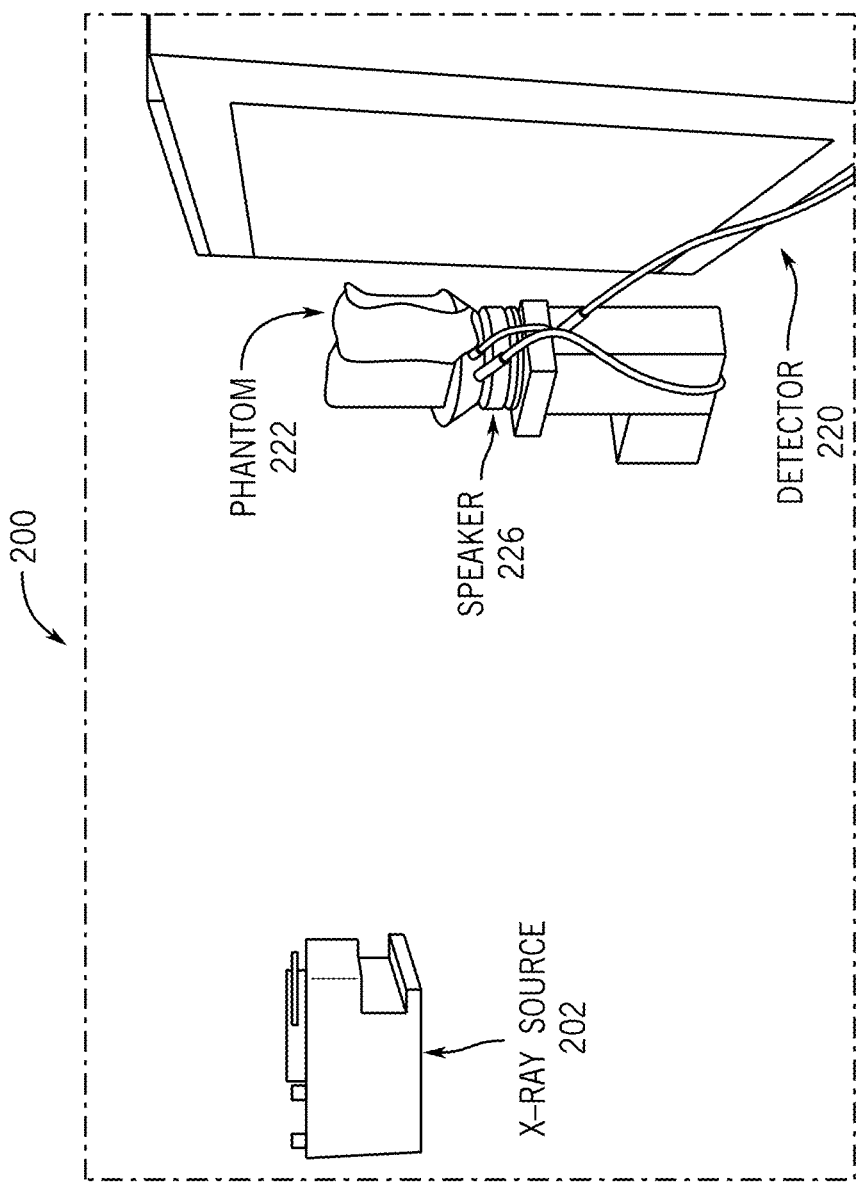
FIG. 2 is a photograph of an example configuration realizing the system of FIG. 1, according to aspects of the present disclosure.

Referring to FIG. 2, an of an experimental setup 200 is provided. The experimental setup 200 was based on the design of the dynamic X-ray elastography setup 100 in FIG. 1 and includes an X-ray source 202, a gel phantom 222 subject to vibration via a speaker 226, a detector 220 for image acquisition, and a control computer (not shown). The continuously acquired 2D images of the phantom subject to the vibration, are post-processed to compute the stiffness maps. The individual components of the experimental setup 200, and the processing steps for deriving the elasticity or stiffness maps, are described below.

According to the present disclosure, an example X-ray source 102 uses an illumination source 104 that includes a pulsed UV LED emitting at 255 nm. The illumination source 104 is placed outside the vacuum manifold of the X-ray source. The light from this illumination source 104 strikes a photocathode 110, which may be a photo-emissive magnesium film, inside the vacuum manifold 108 via a quartz window 106. A number of photoelectrons generated in this matter are amplified by an electron multiplier 112. In one example, a Channeltron™ electron amplifier may be used to amplify by a factor of up to $10^9$. The output electron beam 114 from the Channeltron™ can then be accelerated through a high voltage 115 to strike an anode 116, which in some examples may be a tungsten anode. In one non-limiting example, the optical spot size of the resulting X-ray focal spot is 4.5 mm (horizontal)×1 mm (vertical). The X-ray pulses (and beam current) may be controlled by adjusting the pulse duration, intensity and duty cycle of the illumination source 104 of the X-ray source 102. In one example, seven of such X-ray sources 102 may be housed in a single module and share a common vacuum manifold. The overall 7-element source may be designed to be small and lightweight (approximately 1 kg). The 7 sources may span approximately 24 angular degrees. In one example according to the present disclosure, a single X-ray source 102 was used to generate a pulsed X-ray beam at 30 kVp and 20 μA tube current. The generated X-ray beam was incident upon a phantom mounted on a pneumatic vibration stage described below.

Figure 3:
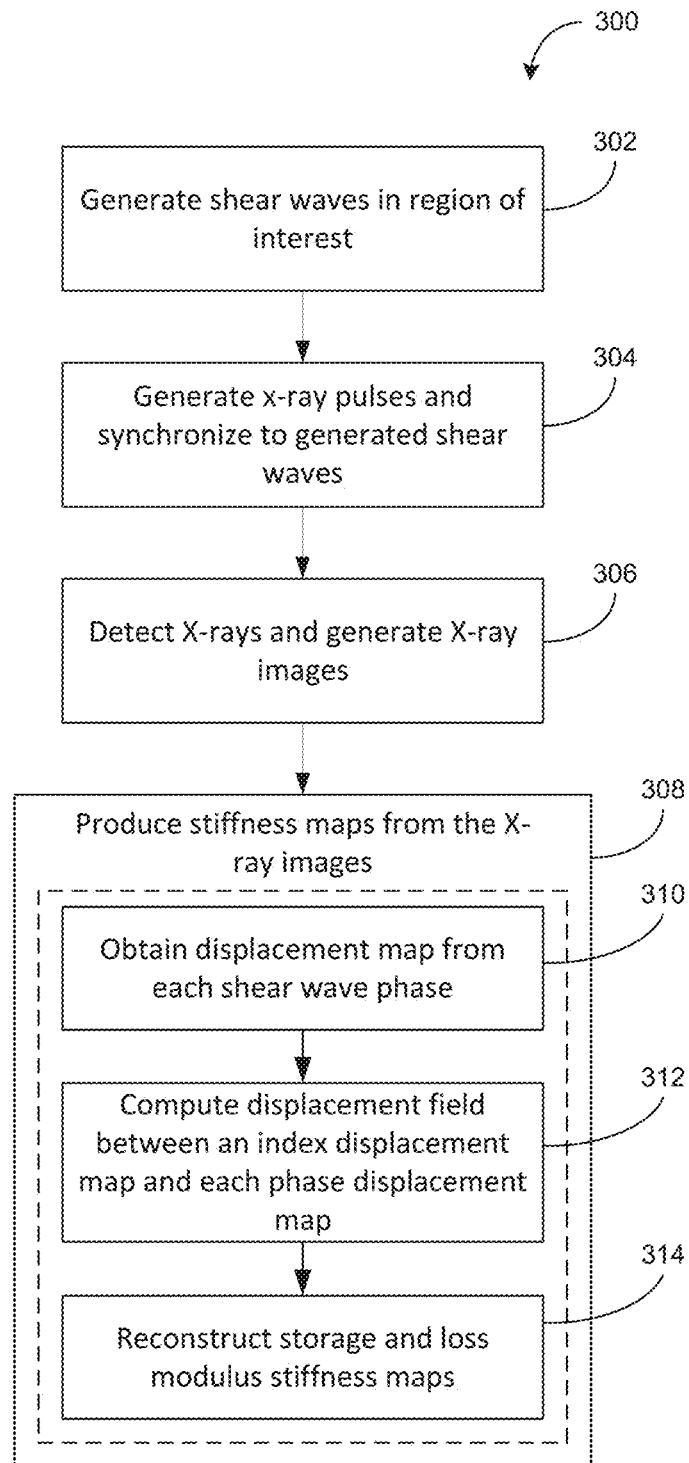
FIG. 3 is a flow chart setting forth some non-limiting example steps of a process for performing dynamic X-ray elastography, according to aspects of the present disclosure.

FIG. 3 is a flow chart setting for a set of non-limiting steps of a workflow according to aspects of the present disclosure. The dynamic X-ray elastography method 300 starts by generating shear waves in a region of interest of a sample in step 302 via a vibration source. Next, the X-ray source generates X-ray pulses that are synchronized to the generated shear waves in step 304. The X-ray pulses are detected by the detector and converted to X-ray images in step 306. As will be described below, a processor performs processing steps to produce stiffness maps from the X-ray images in step 308. In one configuration, the stiffness maps may be two-dimensional (2D) stiffness maps. One non-limiting example producing the stiffness maps is provided in steps 310-314. At step 308, a displacement map from each phase of the shear wave in step 310 is obtained. Next, displacement fields may be computed between an index displacement map (e.g., 0 rad) with each other phase displacement map (e.g., $2/5\pi$, $4/5\pi$, $6/5\pi$, and $8/5\pi$) in step 312. In step 314, storage and loss modulus maps of the sample may be reconstructed from the displacement fields.

The dynamic X-ray elastography method 300 and details of generating the stiffness maps (e.g., at 308 of the method 300) are further described in the non-limiting breast-tomosynthesis example below.

Breast Tomosynthesis Example

Figure 4:
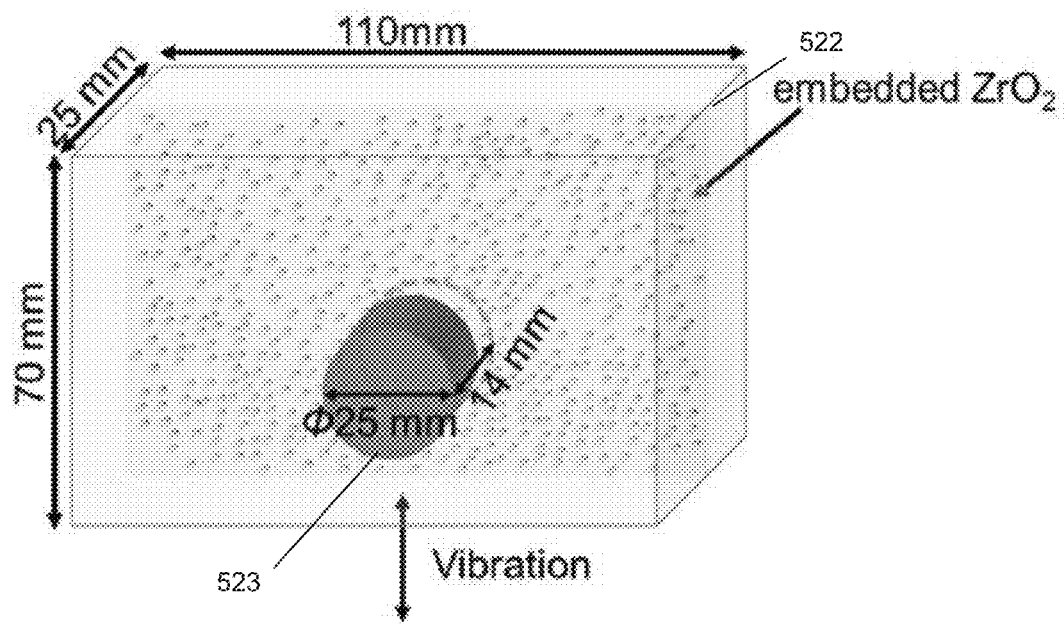
FIG. 4 is a schematic illustration of a phantom used in a non-limiting example workflow of a dynamic X-ray elastography method, according to aspects of the present disclosure.

In an example of breast tomosynthesis system and method in accordance with the present disclosure, a Hitohada gel phantom 522 was prepared (FIG. 4) from soft urethane resin doped with $ZrO_2$ particles to mimic healthy breast tissue. The median grain size distribution of ZrO2 was 89 μm, and 6.3 g of ZrO2 particles were spread over the entire phantom when the phantom was in a liquid state. The phantom had a 25 mm-diameter hard inclusion 523 in the center. Two types of raw materials of clear Hitohada gel were used to make the inclusion and the rest of the phantom: H05-100) (EXSEAL Co. Ltd.) was used for the hard inclusion; H00-100J (EXSEAL Co. Ltd.) was used for the surrounding matrix. These materials have a hardness of Asker-C 7 and Asker-C 0, respectively. The hard inclusion 523 simulated a cancerous lesion with a different elasticity but similar radiolucency. The mass attenuation coefficient of the human breast is roughly 0.690 $cm^2/g$ at an X-ray energy of 20 keV[25]. Assuming a mammary gland density[26] of 1.02 $g/cm^3$, a 2.5 cm thick sample of breast tissue should have an X-ray transmittance on the order of 0.17. The 2.5 cm thick gel phantom used in this experiment had a measured transmittance of 0.15±0.01.

The phantom was pneumatically vibrated using an 8 cm diameter Fostex M800 speaker with an added plastic cover with a 1 mm diameter hole. The sound from the speaker, which induced air pressure wave to vibrate the phantom, was generated by a sinusoidal signal from a data acquisition module or DAQ (National Instruments, USB-6002). The sinusoidal signal from DAQ was amplified using a power amplifier (Bose, Free Space IZA250-LZ) in order to drive the Fostex speaker. The speaker pneumatically vibrated the phantom in the z-direction at a frequency of 115 Hz in order to generate shear waves in the gel. The vibrational acceleration was lower than the limit set by the European Union directive limiting occupational exposure to whole-body and extremity vibrations (2002/44/EC)[27]. With the speaker on, stroboscopic absorption images were acquired at each phase of the vibration to obtain a time-varying, two-dimensional view of the shear wave.

The phantom was illuminated with pulsed X-rays synchronized to the DAQ and the speaker. X-ray images were acquired using a CMOS X-ray flat panel detector (Dexela 2923) that was located 47.4 cm from the X-ray source. The pixel size of the detector was 75 µm×75 µm. The magnification of the phantom was 1.2. Therefore, the effective pixel size at the isocenter of the phantom was 63 µm×63 µm.

Figure 5:
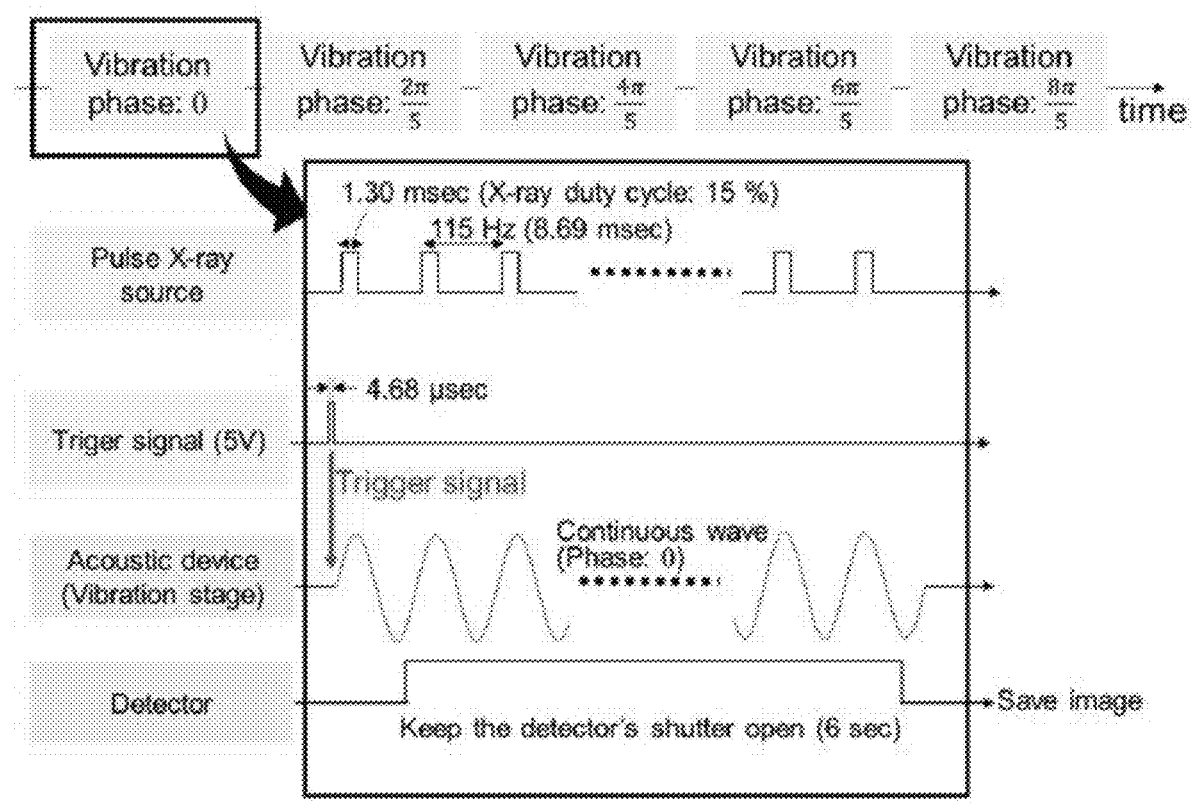
FIG. 5 is a schematic diagram depicting an image acquisition sequence for dynamic X-ray elastography using a pulsed X-ray source, according to aspects of the present disclosure.

The duty cycle of the pulsed X-ray was 15%, with a pulse width of 1.3 ms as shown in FIG. 5. An X-ray projection image of the phantom was accumulated for 6 s, i.e., the electrical shutter of the detector was kept open for this duration. Therefore, the cumulative time for which the phantom was exposed by X-rays to obtain an X-ray projection image was 0.9 s.

The sinusoidal signal from the DAQ was synchronized with X-ray pulses by a trigger from the pulsed X-ray start timing. X-ray projection images were obtained at five different phases of the air pressure vibration: 0, 2/5π, 4/5π, 6/5π, and 8/5π (i.e., 0, 72, 144, 216, and 288 degrees, respectively) with respect to the vibration timing.

To obtain a two-dimensional elasticity map, a three-step process was used that is briefly summarized below[22].

Figure 6:
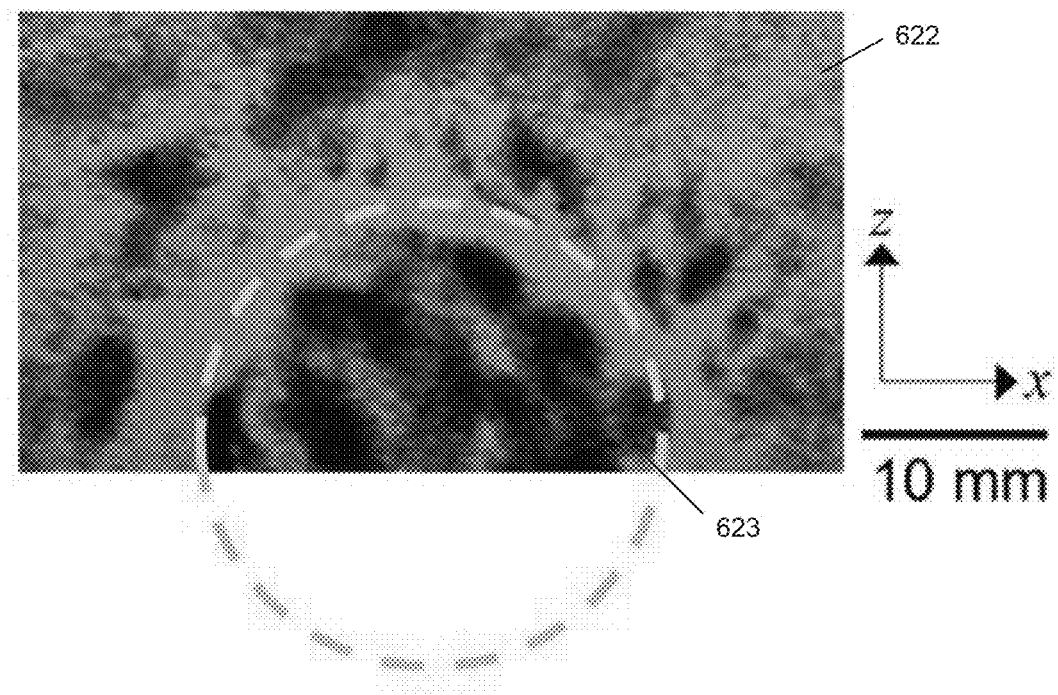
FIG. 6 is an example X-ray attenuation image of a phantom, according to aspects of the present disclosure.

First, the X-ray projection images at the 5 phases (0, 2/5π, 4/5π, 6/5π, and 8/5π) were obtained as shown in FIG. 6. The portion marked by the dotted circle is the hard inclusion embedded in the surrounding matrix.

Displacement maps in the vertical direction (i.e., along the displacement vector of the shear wave) were then obtained as shown in FIGS. 7a-7e. The displacement was retrieved at each pixel in the maps by using a non-rigid registration algorithm—a non-parametric diffeomorphic image registration algorithm based on Thirion's demons algorithm[29]—implemented in MATLAB (Version 9.5.0, The MathWorks, Inc., Natick, MA, USA), and Butterworth bandpass filtering[30] for denoising. The non-rigid registration algorithm, which non-linearly accounts for the local distortion field at each pixel, estimates a displacement field that aligns two images. In this case, the image with 0 rad phase was used as the index image, and the distortion field from it to the images with the phase timing of 2/5π, 4/5π, 6/5π, and 8/5π were computed. The fringe scanning method[31] was applied to this image set and mapped the displacement from the center of vibration amplitude for each pixel as shown in FIGS. 7a-e.

Finally, storage and loss modulus maps for the phantom were reconstructed on the basis of the incompressible algebraic inversion of the differential equation (AIDE)[32] for an incompressible material (∇·u=0, where u is the displacement vector). In the AIDE, the complex shear modulus G is calculated from the wave equation in a stationary state (the Helmholtz equation) as follows:

$$G = -\rho \omega^2 \frac{U_i}{\nabla^2 U_i} \quad (1)$$

Here, ρ is density, ω is angular frequency of vibration, $U_i$ is discrete Fourier transform of $u_i$ with respect to time, where $u_i$ (i=x,y,z) is components of u. The complex shear modulus can be expressed by G=G'+iG", where G'=Re(G) and G"≡Im(G) corresponding to the storage and loss moduli, respectively. As the Poisson's ratio of living tissue is between 0.490 and 0.49933, both the phantom material and human tissue are approximated as incompressible. The volumetric mass density of Hitohada gel was determined to be 1.0 g/cm³. After that, a median filter (25 pixels×25 pixels) was applied to the storage and loss modulus maps to make it smooth.

Figure 7:
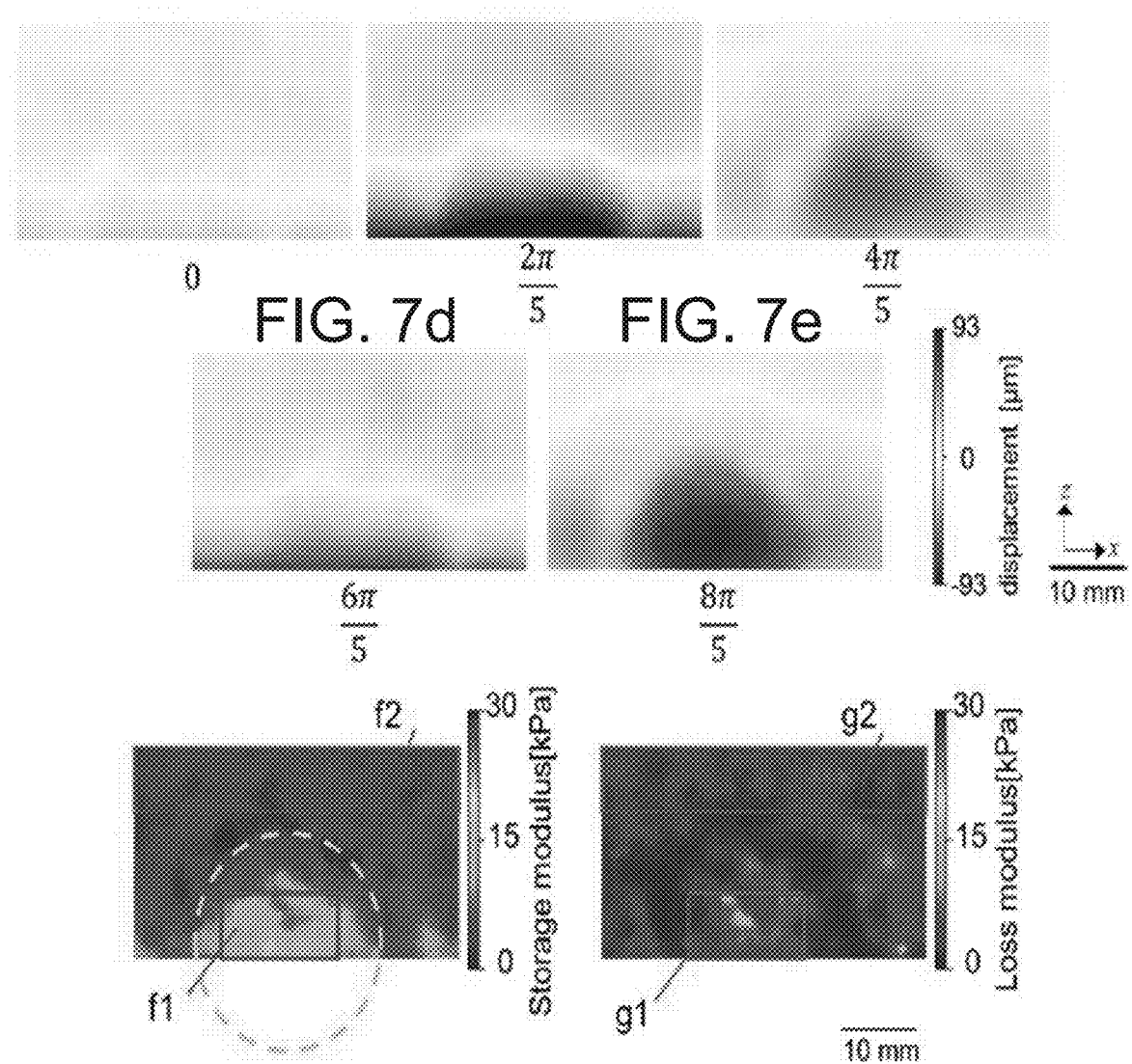
FIGS. 7a-e form a set of displacement maps at phase angles of 0 (FIG. 7a), $2/5\pi$ (FIG. 7b), $4/5\pi$ (FIG. 7c), $6/5\pi$ (FIG. 7d), and 8/5π (FIG. 7e) radians of the phantom described in FIG. 6, respectively.
FIGS. 7f and 7g illustrate stiffness maps of storage and loss moduli, respectively, according to aspects of the present disclosure.

FIGS. 7f and 7g shows the maps of the storage and loss moduli obtained from FIGS. 7a-e. As can be seen, the high storage modulus region corresponds to the region designed to simulate the cancerous lesion; this region has higher elasticity and is denoted by a dotted circle in FIG. 7f. Therefore, the approach is able to distinguish the hard inclusion in a matrix. The storage moduli of the square regions in FIG. 7f denoted (f1) and (f2) were 12±2.5 kPa and 3.4±0.78 kPa, respectively. The loss moduli in the corresponding squares denoted by (g1) and (g2) in FIG. 7g were 4.4±2.1 kPa and 2.8±1.0 kPa, respectively.

The contrast noise ratio (CNR) is calculated as follows:

$$CNR = \sqrt{\frac{2(\bar{S}-\bar{B})^2}{\sigma_S^2 + \sigma_B^2}} \quad (2)$$

Here, $\bar{S}$ and $\bar{B}$ are the mean of the signal and background, $\sigma_S$, and $\sigma_B$ are the standard deviation of the signal and background[34]. "S" is the value measured in the areas of (f1) and (g1) in FIGS. 7f and 7g and "B" is the value measured in (f2) and (g2) in FIGS. 7f and 7g. The CNR in the storage modulus from (f)-1 to (f)-2 was 4.5. On the other hand, the CNR in the transmission image from the same ROI of (f)-1 to (f)-2 was 1.1. As such, the elastography outperforms naïve X-ray transmission imaging in its ability to discriminate a hard inclusion from surrounding material.

The storage and loss moduli were calculated by experiments at a single vibration frequency. However, obtaining results of vibration with multiple frequencies enables examination of how viscosity and elasticity are combined using a model such as the Kelvin-Voigt or Maxwell model[37-39]. Being able to examine viscosity and elasticity of tissues together may allow for more detailed study of disease progression.

The experimental setup and the image processing methods presented above realize X-ray elastography and tomosynthesis in a volumetric fashion. Tomosynthesis with the source module used according to the present disclosure was demonstrated. In one non-limiting implementation the X-ray source had 7 X-ray elements spanning 24 degrees. Therefore, using 3 such sources side-by-side, one can create a 21-element arc of sources spanning approximately 72 degrees. These sources can be electronically steered, and such an assembly can be used for X-ray tomosynthesis without any moving parts. With the help of a vibration stage, it is possible to obtain the projection images over 4 or 5 different phases of shear wave propagation through the tissue. These projection images can then be converted into multiphase tomosynthesis slices, which can then be used to produce slice-by-slice elasticity maps. All imaging for yielding slice-by-slice elasticity maps can be acquired without any moving parts in the setup and without rotating or displacing the sample.

Mammography Application

In mammography, the mean glandular dose (MGD) of full-field Digital Mammography (FFDM) and Digital Breast Tomosynthesis (DBT) for are approximately 1.4 mGy and 1.9 mGy, respectively, for the craniocaudal views as well as the mediolateral oblique views[41]. X-ray elastography can be performed at doses below the European Union and International Atomic Energy Agency MGD limit of 2.5 mGy[42]. The calculated doses were 0.45 mGy for a tissue thickness of 2.5 cm and 0.91 mGy for a clinical mammography exam assuming a tissue thickness of 4 cm. These values were calculated by assuming that the conversion efficiency of the X-rays is 1% of the input, assuming that the X-rays emitted from the target spread out in a spherical shape, ignoring the effects of X-ray absorption and scattering by air, and also ignoring the effects of intensity uniformity in the irradiation field. For X-ray elastography, one can divide this dose budget into lower dose projections that are timed and synchronized with the acoustic vibration according to the schedule described above. As a result, the acquisition of the additional stiffness properties of the breast can essentially be dose neutral both in the FFDM and DBT setups. A possible implementation is depicted in FIG. 8.

Figure 8:
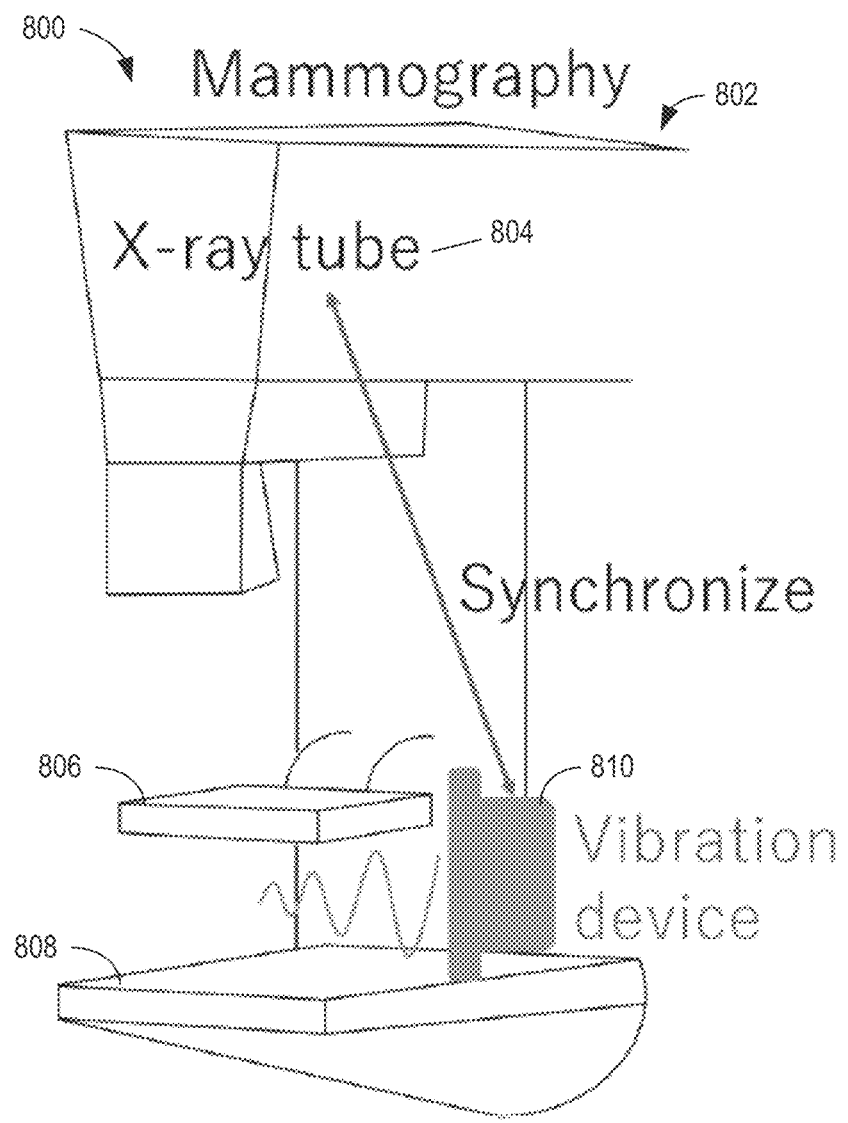
FIG. 8 depicts an example implementation geometry for mammography, according to an aspect of the present disclosure.

In one non-limiting configuration, FIG. 8 depicts a dynamic X-ray elastography mammography system 800 including an X-ray device 802 and an X-ray tube 804, such as the X-ray source 102 of FIG. 1. The system 800 further includes a compression paddle 806 and detector 808. A vibration device 810 is provided adjacent to a sample (not shown) located between the compression paddle 806 and detector 808 to induce shear waves in the sample.

Figure 9:
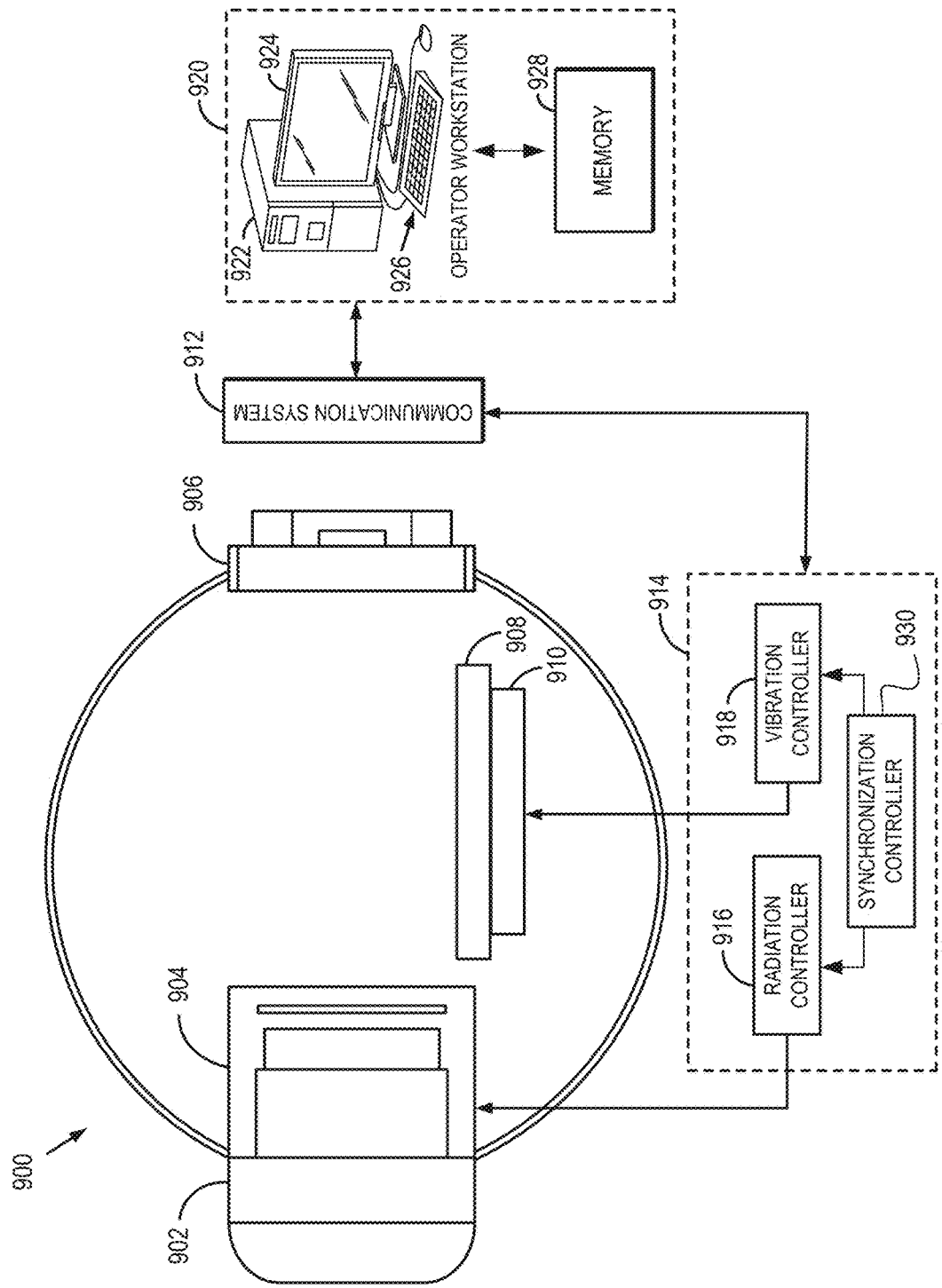
FIG. 9 depicts an example X-ray elastography system for implementation of the dynamic X-ray elastography method, according to aspects of the present disclosure.

Referring now to FIG. 9, an example dynamic X-ray elastography system 900 for a variety of applications is illustrated. The system 900 includes an X-ray source 902 including a vacuum manifold 904 such as that described by the X-ray source 102 of FIG. 1. An X-ray detector 906 is positioned opposite the X-ray source. A stage 908 for supporting a sample (not shown) is positioned between the X-ray source 902 and the manifold 904. A vibration source 910 generates shear waves in the sample. Vibration may be generated pneumatically via a speaker, as in the setup depicted in FIG. 1. Alternatively, the vibration source 910 may actuate the stage 908 to generate shear wave which propagate into the sample.

A controller 914 includes a radiation controller 916 to control the X-ray source 902 to generate pulsed X-rays and a vibration controller 918 for generating a sinusoidal signal from a function generator to drive the vibration source 910 to produce shear waves in the sample.

The controller 914 is connected a communication system 912 which is operatively connected to an operator workstation 920. The operator workstation 920 includes a processor 922, display 924, and user input device 926 such as a keyboard.

In an example configuration, the controller 914 includes a synchronization controller 930 to time the x-ray pulses to different phases of the sinusoidal signal of the shear wave. The radiation controller 916 may further include a switching unit (not shown) for switching on and off an illumination source in the X-ray source 902, such as the illumination source 104 in X-ray source 102 of FIG. 1. The switching unit may include a switching circuitry.

In some configurations, operator workstation 920 can include a processor 922, a display 924, one or more inputs 926, connected to one or more communication systems 912. In some configurations, processor 922 can be any suitable hardware processor or combination of processors, such as a central processing unit ("CPU"), a graphics processing unit ("GPU"), and so on. In some configurations, display 924 can include any suitable display devices, such as a liquid crystal display ("LCD") screen, a light-emitting diode ("LED") display, an organic LED ("OLED") display, an electrophoretic display (e.g., an "e-ink" display), a computer monitor, a touchscreen, a television, and so on. In some configurations, inputs 926 can include any suitable input devices and/or sensors that can be used to receive user input, such as a keyboard, a mouse, a touchscreen, a microphone, and so on.

In some configurations, memory 928 can include any suitable storage device or devices that can be used to store instructions, values, data, or the like, that can be used, for example, by processor 922 to present content using display 924, to communicate with operator workstation 920 via communications system(s) 912, and so on. Memory 928 can include any suitable volatile memory, non-volatile memory, storage, or any suitable combination thereof. For example, memory 928 can include random-access memory ("RAM"), read-only memory ("ROM"), electrically programmable ROM ("EPROM"), electrically erasable ROM ("EEPROM"), other forms of volatile memory, other forms of non-volatile memory, one or more forms of semi-volatile memory, one or more flash drives, one or more hard disks, one or more solid state drives, one or more optical drives, and so on. In some configurations, memory 928 can have encoded thereon, or otherwise stored therein, a computer program for controlling operation of operator workstation 920. In such configurations, processor 922 can execute at least a portion of the computer program to present content (e.g., images, user interfaces, graphics, tables). For example, the processor 922 and the memory 928 can be configured to perform the methods described herein (e.g., the method of FIG. 3).

In some configurations, communications systems 912 can include any suitable hardware, firmware, and/or software for communicating information over communication network 1054 and/or any other suitable communication networks. For example, communications system 912 can include one or more transceivers, one or more communication chips and/or chip sets, and so on. In a more particular example, communications system 912 can include hardware, firmware, and/or software that can be used to establish a Wi-Fi connection, a Bluetooth connection, a cellular connection, an Ethernet connection, and so on.

Referring now to FIG. 10, an example of a system 1000 for performing dynamic x-ray elastography in accordance with some configurations of the systems and methods described in the present disclosure is shown. As shown in FIG. 10, a computing device 1050 can receive one or more types of data (e.g., X-ray images from a radiograph system, previously generated X-ray data, and so on) from data source 1002. In some configurations, computing device 1050 can execute at least a portion of the dynamic x-ray elastography system 1004 to generate stiffness maps from a sample subject to synchronized x-ray irradiation pulses and vibration for shear waves generation using data received from the data source 1002.

Additionally or alternatively, in some configurations, the computing device 1050 can communicate information about data received from the data source 1002 to a server 1052 over communication network 1054, which can execute at least a potion of the dynamic x-ray elastography system 1004. In such configurations, the server 1052 can return information to the computing device 1050 (and/or any suitable computing device) indicative of an output of the dynamic x-ray elastography system 1004.

In some configurations, computing device 1050 and/or server 1052 can be any suitable computing device or combination of devices, such as a desktop computer, a laptop computer, a smartphone, a tablet computer, a wearable computer, a server computer, a virtual machine being executed by a physical computing device, and so on.

In some configurations, data source 1002 can be any suitable source of data (e.g., X-ray images, computed tomography (CT) images, elastography images), such as an x-ray elastography system, another computing device (e.g., a server storing x-ray data, CT data, elastography data), and so on. In some configurations, data source 1002 can be local to computing device 1050. For example, data source 1002 can be incorporated with computing device 1050 (e.g., computing device 1050 can be configured a part of a device for measuring, recording, estimating, acquiring, or otherwise collection or storing data). As another example, data source 1002 can be connected to computing device 1050 by a cable, a direct wireless link, and so on. Additionally or alternatively, in some configurations, data source 1002 can be located locally and/or remotely from computing device 1050, and can communicate data to computing device 1050 (and/or server 1052) via a communication network (e.g., communication network 1054).

In some configurations, communication network 654 can be any suitable communication network or combination of communication networks. For example, communication network 654 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), other types of wireless network, a wired network, and so on. In some configurations, communication network 654 can be a local area network, a wide area network, a public network (e.g., the Internet), a private or semi-private network (e.g., a corporate or university intranet), any other suitable type of network, or any suitable combination of networks. Communications links shown in FIG. 6 can each be any suitable communications link or combination of communications links, such as wired links, fiber optic links, Wi-Fi links, Bluetooth links, cellular links, and so on.

As used herein in the context of computer implementation, unless otherwise specified or limited, the terms "component," "system," "module," "controller," "framework," and the like are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

In some implementations, devices or systems disclosed herein can be utilized or installed using methods embodying aspects of the disclosure. Correspondingly, description herein of particular features, capabilities, or intended purposes of a device or system is generally intended to inherently include disclosure of a method of using such features for the intended purposes, a method of implementing such capabilities, and a method of installing disclosed (or otherwise known) components to support these purposes or capabilities. Similarly, unless otherwise indicated or limited, discussion herein of any method of manufacturing or using a particular device or system, including installing the device or system, is intended to inherently include disclosure, as embodiments of the disclosure, of the utilized features and implemented capabilities of such device or system.

As used herein, the phrase "at least one of A, B, and C" means at least one of A, at least one of B, and/or at least one of C, or any one of A, B, or C or combination of A, B, or C. A, B, and C are elements of a list, and A, B, and C may be anything contained in the Specification.

The present disclosure has described one or more preferred embodiments, and it should be appreciated that many equivalents, alternatives, variations, and modifications, aside from those expressly stated, are possible and within the scope of the invention.

The invention claimed is:

1. A method for performing dynamic X-ray elastography, the method comprising:
controlling a vibration source to generate shear waves in a region of interest of a subject;
controlling an X-ray source to direct a series of X-ray pulses, pulsed at a predetermined frequency, toward the region of interest of the subject, wherein the predetermined frequency is synchronized to a selected phase of the shear waves;
detecting the X-ray pulses using an X-ray detector to acquire X-ray data;
generating, using a processor, stiffness maps from the X-ray data; and
displaying, using a display, the stiffness maps.

2. The method of claim 1, wherein controlling the X-ray source includes using a controller to switch on and off a radiation source in the X-ray source at the predetermined frequency.

3. The method of claim 1, wherein generating the stiffness maps further comprises determining a storage modulus and a loss modulus using the X-ray data by generating X-ray images from the X-ray data, wherein each of the X-ray images is associated with a displacement of the region of interest based on a phase of the shear wave.

4. The method of claim 2, wherein the radiation source includes an ultraviolet (UV) light emitting diode (LED), a photocathode, or an electron amplifier.

5. The method of claim 2, wherein the radiation source includes a carbon nanotube forming a cathode.

6. The method of claim 2, wherein the radiation source includes a silicon field emitter forming a cathode.

7. The method of claim 3, wherein generating the stiffness maps comprises:
(a) generating displacement maps from each X-ray image associated with a phase of the shear wave;
(b) setting an index displacement map from one of the shear wave phases;
(c) computing displacement fields between the index displacement map and each additional shear wave displacement map; and
(d) reconstructing storage and loss modulus stiffness maps from the displacement fields.

8. The method of claim 7, further comprising:
denoising the displacement maps using a Butterworth bandpass filter; and
minimizing displacement field distortion using a non-rigid registration algorithm.

9. An apparatus for performing dynamic X-ray elastography, the apparatus comprising:
a vibration source;
an X-ray source;
an X-ray detector;
a controller configured to drive the vibration source to generate shear waves in a region of interest of a subject and drive the X-ray source to generate and direct X-ray pulses, pulsed at a predetermined frequency, toward the region of interest of the subject, wherein the predetermined frequency is synchronized to selected phases of the shear waves;

a processor configured to generate one or more X-ray images from X-ray data acquired by the X-ray detector and generate stiffness maps from the one or more X-ray images; and a display configured to display the stiffness maps.

10. The apparatus of claim 9, wherein the X-ray source includes an illumination source, and wherein the controller is further configured to switch on and off the illumination source in the X-ray source at the predetermined frequency.

11. The apparatus of claim 9, wherein the stiffness maps include a map of a storage modulus and a loss modulus based on the X-ray images, wherein each of the X-ray images is associated with a displacement of the region of interest based on one of the selected phases of the shear waves.

12. The apparatus of claim 10, wherein the illumination source includes a UV LED, a photocathode, or an electron amplifier.

13. The apparatus of claim 10, wherein the illumination source includes a carbon nanotube forming a cathode.

14. The apparatus of claim 10, wherein the illumination source includes a silicon field emitter forming a cathode.

15. The apparatus of claim 11, wherein the stiffness maps are generated by
  (a) generating displacement maps from each X-ray image associated with a phase of the shear wave;
  (b) setting an index displacement map from one of the shear wave phases;
  (c) computing displacement fields between the index displacement map and each additional shear wave displacement map; and
  (d) reconstructing storage and loss modulus stiffness maps from the displacement fields.

16. The apparatus of claim 15, further comprising:
denoising the displacement maps using a Butterworth bandpass filter; and
minimizing displacement field distortion using a non-rigid registration algorithm.

17. A method for performing dynamic X-ray elastography, the method comprising:
  controlling a vibration source to generate shear waves in a region of interest of a subject;
  controlling an X-ray source to direct a series of X-ray pulses toward the region of interest of the subject, wherein the X-ray pulses are synchronized with the shear waves;
  detecting the X-ray pulses using an X-ray detector to acquire X-ray data;
  generating, using a processor, stiffness maps from the X-ray data,
    wherein generating the stiffness maps further comprises determining a storage modulus and a loss modulus using the X-ray data by generating X-ray images from the X-ray data, wherein each of the X-ray images is associated with a displacement of the region of interest based on a phase of the shear wave; and
  displaying, using a display, the stiffness maps.

18. An apparatus for performing dynamic X-ray elastography, the apparatus comprising:
  a vibration source;
  an X-ray source;
  an X-ray detector;
  a controller configured to drive the vibration source to generate shear waves in a region of interest of a subject and drive the X-ray source to generate and direct X-ray pulses toward the region of interest of the subject, wherein the X-ray pulses are synchronized with the shear waves;
  a processor configured to generate one or more X-ray images from X-ray data acquired by the X-ray detector and generate stiffness maps from the one or more X-ray images,
    wherein the stiffness maps include a map of a storage modulus and a loss modulus based on the X-ray images, wherein each of the X-ray images is associated with a displacement of the region of interest based on a phase of the shear wave; and
  a display configured to display the stiffness maps.

* * * * *